US00PP34469P2

(12) United States Plant Patent
Thiede

(10) Patent No.: US PP34,469 P2
(45) Date of Patent: Aug. 2, 2022

(54) ***DIANTHUS* PLANT NAMED 'KLEDP22351'**

(50) Latin Name: *Dianthus caryophyllus*
Varietal Denomination: KLEDP22351

(71) Applicant: Klemm+Sohn GmbH & Co. KG, Stuttgart (DE)

(72) Inventor: Lena Thiede, Riederich (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 17/583,565

(22) Filed: Jan. 25, 2022

(51) Int. Cl.
*A01H 5/02* (2018.01)
*A01H 6/30* (2018.01)

(52) U.S. Cl.
USPC ..... Plt./281
CPC ..... *A01H 6/305* (2018.05)

(58) Field of Classification Search
USPC ..... Plt./281
CPC ..... A01H 6/305; A01H 5/02
See application file for complete search history.

*Primary Examiner* — Keith O. Robinson
(74) *Attorney, Agent, or Firm* — Weatherly IP Solutions, LLC; Barbara Campbell

(57) ABSTRACT

A new *Dianthus* plant designated 'KLEDP22351' particularly distinguished by double light pink flowers having pink centers, a compact growth habit, and an upright plant habit, is disclosed.

1 Drawing Sheet

Genus and species: *Dianthus caryophyllus*.
Variety denominations: 'KLEDP22351'.

BACKGROUND OF THE NEW PLANT

The present invention comprises a new and distinct variety of *Dianthus*, botanically known as *Dianthus* cultivars, and hereinafter referred to by the variety name 'KLEDP22351'. 'KLEDP22351' originated from a naturally-occurring, whole plant mutation from the *Dianthus* parent 'KLEDP07089' (Unpatented) in April 2016 in The Netherlands.

In August 2016, 'KLEDP22351' was first vegetatively propagated by vegetative stem cuttings in Stuttgart, Germany. 'KLEDP22351' was found to reproduce true to type in successive generations of asexual propagation in Latina, Italy and Stuttgart, Germany via vegetative cuttings.

SUMMARY

The following are the most outstanding and distinguishing characteristics of 'KLEDP22351' when grown under normal horticultural practices in Stuttgart, Germany.

1. Double light pink flowers having pink centers;
2. A compact growth habit; and
3. An upright plant habit.

DESCRIPTION OF THE PHOTOGRAPH

This new *Dianthus* plant is illustrated by the accompanying photograph of a 14-week-old plant taken in May 2017 and grown in a greenhouse in Stuttgart, Germany. The colors shown are as true as can be reasonably obtained by conventional photographic procedures. The photograph is a whole plant photo of 'KLEDP22351' and shows the foliage, buds, and flowers.

DESCRIPTION

The following detailed descriptions set forth the distinctive characteristics of 'KLEDP22351'. The data which define these characteristics were collected from asexual reproductions carried out in Stuttgart, Germany. Data was collected in November 2021 on plants 23 weeks after potting and grown in a plastic greenhouse. Color references are to The R.H.S. Colour Chart of The Royal Horticultural Society of London (R.H.S.), 5$^{th}$ edition (2007).

Classification:
- *Family*.—Caryophyllaceae.
- *Botanical*.—*Dianthus caryophyllus*.
- *Designation*.—'KLEDP22351'.

Parentage: Mutation parent 'KLEDP07089' (Unpatented).

Plant:
- *Propagation type*.—Vegetative cuttings.
- *Time to produce a rooted young plant*.—4 weeks.
- *Root description*.—Fine and white, RHS 155A.
- *Rooting habit shape*.—Lanceolate.
- *Plant form*.—Upright.
- *Plant height*.—14 cm.
- *Plant diameter or spread*.—18 cm.

Lateral branches/stems:
- *Shape of the branch in cross-section*.—Circular.
- *Hollowness of the branch*.—Absent.
- *Length*.—13 cm.
- *Diameter*.—0.2 cm.
- *Internode length*.—2 cm.
- *Internode quantity per branch*.—5 to 8.
- *Node length*.—0.2 cm.
- *Node diameter*.—0.3 cm.
- *Texture*.—Smooth.
- *Color*.—RHS 137A (Green).
- *Flower clustering on the lateral branch*.—In some lateral branches.

Foliage:
- *Arrangement*.—Opposite.
- *Length*.—5.5 cm.
- *Width*.—0.6 cm.
- *Shape*.—Obovate.
- *Apex*.—Acute.

*Base*.—Obtuse.
*Margin*.—Entire.
*Texture* (*both upper and lower surfaces*).—Smooth.
*Cross-section of the leaf*.—Moderately concave.
*Curvature of the leaf*.—Absent.
*Glaucosity of the leaf*.—Weak.
*Leaf color* (*both immature and mature*).—Upper surface: RHS 144A (Yellow-Green) for immature and RHS N137A (Green) for mature. Lower surface: RHS 144A (Yellow-Green) for immature and RHS 137A (Green) for mature.
*Venation pattern*.—Parallel.
*Venation color* (*for both upper and lower surfaces*).—RHS 137A (Green).

Flowers:
*Flower type and habit*.—Double, small sprays, round.
*Fragrance*.—Present; fresh and slight.
*Position of the flowers compared to the foliage of the plant*.—Same level.
*Profile of both the upper and lower part in the lateral view*.—Flat convex.
*Natural flowering season*.—Spring to Fall.
*Flower longevity on the plant*.—10 to 15 days.

Buds:
*Length*.—1.3 cm.
*Diameter*.—0.7 cm.
*Shape*.—Oblong.
*Color*.—RHS 138A (Green).
*Extrusion of the styles at the bud stage*.—Absent.

Corolla:
*Quantity of petals and arrangement*.—16 and arranged in several whorls.
*Corolla height*.—1.5 cm.
*Petal length*.—3.3 cm.
*Petal width*.—2.0 cm.
*Petal shape*.—Obtuse.
*Petal apex*.—Obtuse.
*Petal base*.—Acute.
*Petal margin*.—Crenate.
*Depth of petal margin*.—Shallow.
*Petal texture* (*both upper and lower surfaces*).—Smooth.
*Petal color* (*mature*).—Upper surface: RHS 65B (Red-Purple) with RHS 73A (Red-Purple) centers. Lower surface: RHS 69D (Red-Purple) and RHS 76B (Purple).
*Macule*.—Present; 1.5 cm to 1.8 cm wide and RHS 72A (Red-Purple).
*Calyx*.—Quantity of sepals and arrangement: Composed of 5 sepals. Longitudinal axis of the lobes of the calyx: Straight. Shape: Cylindrical. Calyx height: 1.8 cm. Calyx diameter (at the apex): 0.9 cm. Sepal texture (both upper and lower surfaces): Smooth. Sepal color: Upper surface: RHS 144A (Yellow-Green). Lower surface: RHS 145B (Yellow-Green).
*Position of the outer lobes of the epicalyx in relation to the calyx*.—Adpressed.
*Apex shape of the outer lobes of the epicalyx*.—Acute.
*Apex shape of the inner lobes of the epicalyx*.—Short acuminate.

Peduncles:
*Length*.—1.8 cm.
*Diameter*.—0.2 cm.
*Strength*.—Medium.
*Texture*.—Smooth.
*Color*.—RHS 137A (Green).

Reproductive organs:
*Stamens*.—Quantity per flower: 6. Filament length: 0.9 cm. Filament color: RHS 145B (Yellow-Green). Anther length: 0.1 cm. Anther diameter: 0.1 cm. Anther color: RHS 162 (Greyed-Yellow). Pollen amount: None observed.
*Pistils*.—Quantity per flower: 6. Length: 1.7 cm. Diameter: Less than 0.1 cm. Stigma: Color: RHS 155C (White). Shape: Filamentous. Length: 0.2 cm. Diameter: Less than 0.1 cm. Style: Color: RHS 155C (White). Length: 0.2 cm. Diameter: Less than 0.1 cm. Ovary: Color: RHS 145C (Yellow-Green). Shape: Oblong. Length: 1.1 cm.

Fruit and seed set: Sometimes observed but no information is available.

Disease and pest/insect resistance: No disease and pest/insect resistance observed.

COMPARISON OF 'KLEDP22351' WITH PARENTAL LINE AND KNOWN VARIETY

'KLEDP22351' is distinguished from the mutation parent as described in Table 1.

TABLE 1

Comparison with Parental Line

| Characteristic | 'KLEDP22351' | Mutation Parent 'KLEDP07089' |
|---|---|---|
| Flower color | Light-pink with pink centers | Pink with purple centers |

'KLEDP22351' can be compared to the commercial *Dianthus* variety 'KLEDP07088' (Unpatented). Differences between the varieties are described in Table 2.

TABLE 2

Comparison with Similar Variety

| Characteristic | 'KLEDP22351' | 'KLEDP07088' |
|---|---|---|
| Flower color | Light-pink with pink centers | Purple with white pattern |
| Growth Habit | Compact Upright | Medium Semi-upright |

I claim:

1. A new and distinct variety of *Dianthus* plant designated 'KLEDP22351' as illustrated and described herein.

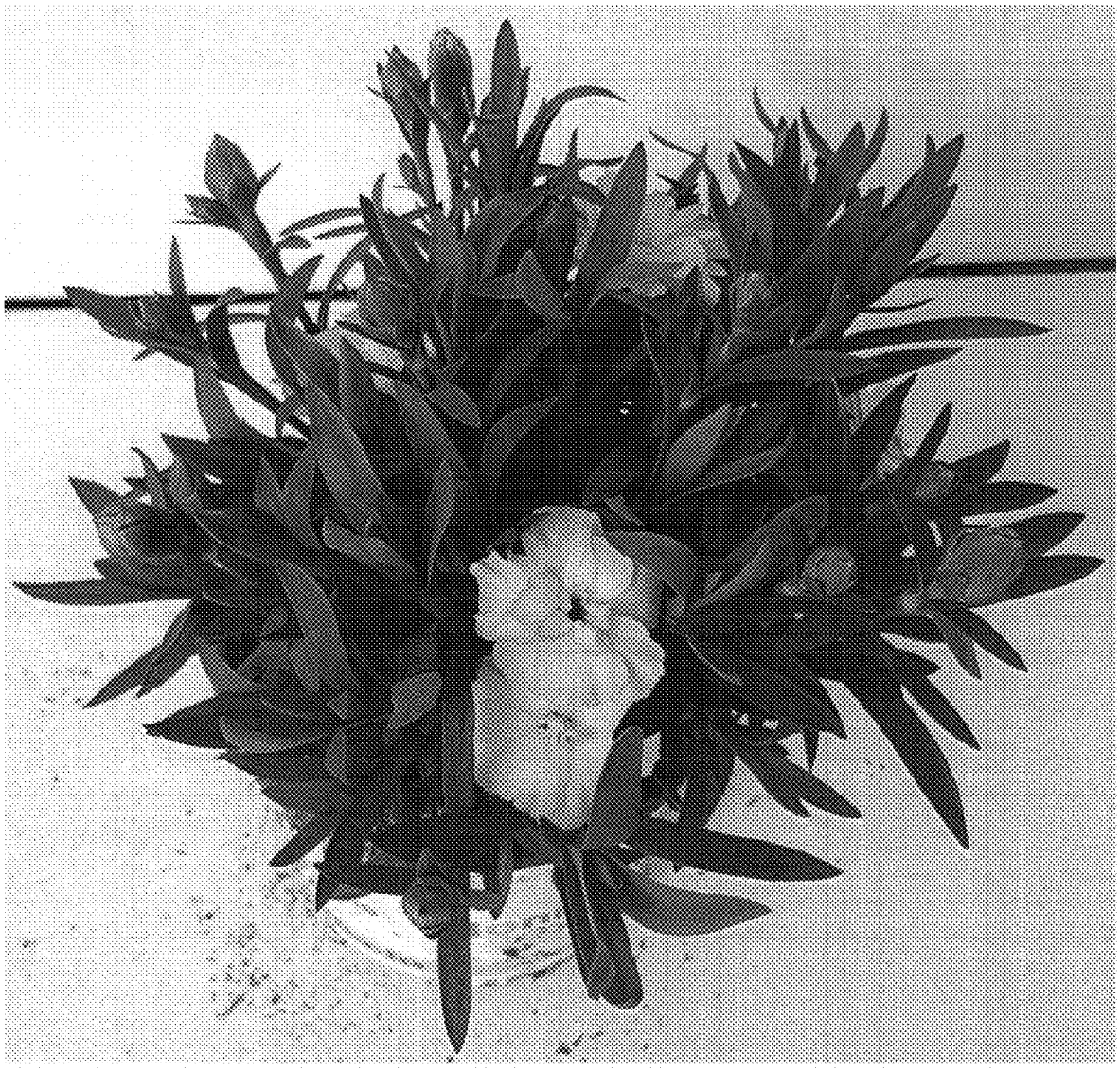

* * * * *